United States Patent [19]

Randen

[11] Patent Number: 4,552,755
[45] Date of Patent: Nov. 12, 1985

[54] SUBSTANTIVE MOISTURIZING COMPOSITIONS

[75] Inventor: Neil A. Randen, Stillwater, Minn.

[73] Assignee: Minnesota Mining and Manufacturing Company, St. Paul, Minn.

[21] Appl. No.: 611,730

[22] Filed: May 18, 1984

[51] Int. Cl.$^4$ ...................... A61K 31/78; A61K 47/00
[52] U.S. Cl. .................................... 424/81; 514/785; 514/938; 514/195.1
[58] Field of Search .......................... 424/358, 81, 168

[56] References Cited

U.S. PATENT DOCUMENTS

| 3,911,105 | 10/1975 | Papantoniou et al. | 424/78 |
| 4,057,622 | 11/1977 | Hase et al. | 424/78 |
| 4,057,623 | 11/1977 | Hase et al. | 424/78 |
| 4,057,624 | 11/1977 | Hase et al. | 424/78 |
| 4,128,634 | 12/1978 | Hase et al. | 424/81 |
| 4,128,635 | 12/1978 | Hase et al. | 424/81 |
| 4,128,636 | 12/1978 | Hase et al. | 424/81 |
| 4,172,122 | 10/1979 | Kubik et al. | 424/59 |
| 4,223,009 | 9/1980 | Chakrabarti | 424/70 |
| 4,272,511 | 6/1981 | Papantoniou et al. | 424/70 |
| 4,335,103 | 6/1982 | Barker et al. | 424/81 |
| 4,348,380 | 9/1982 | Jacquet et al. | 424/81 |
| 4,364,930 | 12/1982 | Griat et al. | 424/81 |
| 4,423,031 | 12/1983 | Murui et al. | 424/81 |

FOREIGN PATENT DOCUMENTS

| 0074191 | 3/1983 | European Pat. Off. | 424/70 |
| 54-151139 | 11/1979 | Japan | 424/358 |
| 55-130907 | 10/1980 | Japan | 424/63 |
| 0090006 | 7/1981 | Japan | 424/70 |
| 0104809 | 8/1981 | Japan | 424/70 |

Primary Examiner—Dale R. Ore
Attorney, Agent, or Firm—Donald M. Sell; James A. Smith; Carolyn A. Bates

[57] ABSTRACT

Improved, oil-in-water moisturizing compositions are disclosed comprising an oil phase containing at least one emollient oil and an oil-soluble acrylate polymer, a water phase and an emulsifying agent. The acrylate polymer improves the substantivity of the compositions.

6 Claims, No Drawings

SUBSTANTIVE MOISTURIZING COMPOSITIONS

TECHNICAL FIELD

This invention relates to moisturizing compositions for the treatment and prevention of dry skin. More specifically, it relates to moisturizing compositions of the oil-in-water emulsion type.

BACKGROUND ART

Dry skin is one of the most significant cosmetic problems in today's population. It is caused by a reduction in both the water content and the lipid content of the skin. The two main approaches which have been taken in the past to moisturize skin are: (1) to apply compositions containing hygroscopic materials to the skin in order to attract and hold water on the skin's surface, and (2) to apply compositions containing oily materials which form a barrier on the skin and thereby reduce transepidermal water loss through the skin. In the latter case, the water level is thought to build up in the skin layer beneath the barrier. Today, the most accepted approach to moisturization involves the use of both methods simultaneously. Most of the moisturizing products in the marketplace today consist of oil-in-water emulsions and creams, water-in-oil emulsions and, to a lesser degree, simply 100% oil formulations. These compositions generally use oils as the main moisturizing ingredient with lesser amounts of humectants. The oils are selected from a large group of commercially available, cosmetically accepted oils, which are generally recognized by the cosmetic industry as having emollient properties.

While these moisturizing products do work, their effects are not long-lasting, i.e., they have to be used repeatedly in order to provide a maximum moisturizing benefit. This is primarily due to the fact that the moisturizing oils do not remain on the skin's surface long enough. Surfactants present in the compositions tend to increase their water-removability.

According to the present invention, it has been discovered that certain oil-soluble acrylate polymers, in combination with conventional moisturizing oils, in an oil-in-water emulsion, provide improved cosmetically-acceptable moisturizing compositions which are substantive to skin, i.e., they are not readily removed by simple abrasion or water assault.

Oil-soluble acrylate polymers have been used heretofore in sunscreening compositions of the oil or water-in-oil type to reduce removal of the sunscreening agent from the skin by swimming or perspiration. Such compositions are described in U.S. Pat. No. 4,172,122.

Other cosmetic compositions containing oil-soluble acrylate polymers include make-up compositions such as lip rouges and mascara disclosed in U.S. Pat. No. 3,911,105, eyeliners and mascaras disclosed in Japanese Patent Application (Publication No.) 54-151139; and eyeliners disclosed in Japanese Patent Application (Publication No.) 55-130907.

Water-in-oil emulsion compositions for skin treatment containing low molecular weight oil-soluble acrylate copolymers as emulsifying agents are disclosed in U.S. Pat. Nos. 4,057,622; 4,057,623; 4,057,624; 4,128,634; 4,128,635; 4,128,636. However, prior to the present invention, it had not been recognized that the addition of certain oil-soluble acrylate polymers to oil-in-water emulsions containing emollient oils and surfactants results in compositions having improved, long-lasting skin moisturizing effects.

SUMMARY OF THE INVENTION

According to the present invention, there is provided an improved oil-in water emulsion for the treatment and prevention of dry skin containing an oil phase comprising at least one emollient oil and an effective amount of an oil-soluble acrylate polymer having a solubility parameter of 6 to 10 $(cal/cc)^{\frac{1}{2}}$ in poorly hydrogen-bonding solvents, a water phase and, an emulsifying agent. Emulsions of the invention have a substantivity value (as hereinafter defined) of at least 30.

The term "acrylate polymer" as used herein to define the polymers useful in the practice of the invention refers to homopolymers, copolymers, terpolymers, etc. derived from the polymerization of at least one ester monomer of formula 1 below:

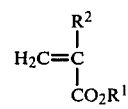
Formula 1 wherein
$R^1$ is an alkyl radical containing 4 to 18 carbon atoms in cyclic, straight- or branched-chain configuration; and
$R^2$ is hydrogen or lower alkyl.

The term "lower alkyl" refers to an alkyl radical containing one to four carbon atoms.

The polymer may optionally contain up to 30 mole percent of the same or different monomers of formula 2 below:

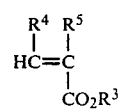
Formula 2 wherein $R^3$ is H or an alkyl group containing 1 to 18 carbon atoms; $R^4$ is hydrogen, methyl, or $-CO_2R^3$, and $R^5$ is hydrogen, lower alkyl or $-CH_2CO_2R^3$; provided when $R^4$ is not hydrogen, $R^5$ is hydrogen and when $R^5$ is not hydrogen, $R^4$ is hydrogen. When difunctional acid monomers only are included along with an ester monomer of formula 1, the mole percent of such acid monomers should not exceed about 15 in order to maintain the required solubility parameter.

The term "emollient oil" as used herein refers to any cosmetically-acceptable oil or mixture of oils which forms a barrier on the skin capable of retarding the evaporation of water.

The term "substantivity value" is used herein to refer to the value obtained when a test composition is subjected to the substantivity test described in detail hereinbelow. Basically, the substantivity value refers to the percentage of the test composition remaining on the skin following a water assault of prescribed magnitude and duration.

Compositions of the present invention have a substantivity value of at least 30, and for the preferred compositions, the value is much higher. They exhibit improved skin moisturizing properties which may be due, in part, to the surprising moisturizing effect of the acrylate polymer itself, as well as the fact that the presence of the acrylate polymer enables the composition to remain on the skin longer.

DETAILED DESCRIPTION OF THE INVENTION

The improved moisturizing compositions of the present invention are oil-in-water emulsions having an oil-soluble acrylate polymer incorporated into the oil phase along with emollient oils.

The emollient oil used in the compositions may be any oil or mixture of oils which is conventionally used in the cosmetic art and which retards the evaporation of water from the skin. Examples of suitable oils include saturated fatty esters and diesters such as isopropyl palmitate, isopropyl myristate, butyl stearate, diisopropyl adipate, dioctyl sebacate, propylene glycol dipelargonate, etc., paraffin oils and waxes, animal and vegetable oils including mink oil, coconut oil and derivatives, palm oil, corn oil, cocoa butter, sesame oil, and the like, lanolin derivatives, fatty alcohols such as isostearyl alcohol, isocetyl alcohol, and straight chain alcohols from $C_6$-$C_{18}$, and certain petroleum distillates which are toxicologically safe such as $C_8$-$C_{18}$ isoparaffin hydrocarbon solvents. The oils mentioned in this list are merely examples and are not intended to limit the invention in any way. In general, any nonvolatile material or mixture thereof which is toxicologically safe for human use and which has a solubility parameter in the range of 6 to 10 (cal/cc)$^{\frac{1}{2}}$ in poorly hydrogen-bonding solvents may be used as the emollient oil in the compositions of the invention.

Emollient oils which have proved to be useful in the compositions include petrolatum, cetyl palmitate, cetyl/stearyl alcohol, propylene glycol, dicaprylate/dicaprate, 15 mole propoxylate of stearyl alcohol, silicone fluids, 2 mole propoxylate of myristyl propionate.

The acrylate polymers used in the compositions can be prepared from the corresponding alkyl esters of acrylic acid, methacrylic acid, etc., wherein the ester alkyl groups may contain 4 to 18 carbon atoms and are exemplified by butyl, iso-amyl, n-hexyl, 2-ethylhexyl, iso-octyl, iso-decyl, lauryl, octadecyl, stearyl groups and the like. Esters wherein the alkyl group contain less than four carbon atoms may be included in small amounts, e.g., less than 10 mole percent. However, in order to achieve the requisite solubility parameter, the polymers should generally not contain a significant amount of lower alkyl ester monomers.

The acrylate polymers may optionally contain up to 30 mole percent of the unesterified a,β-olefinically unsaturated carboxylic acids of Formula II such as acrylic acid, methacrylic acid, maleic acid or itaconic acid, provided the resulting polymer exhibits the requisite solubility parameter. The presence of the carboxylic acid monomer increases the removability of the compositions with soap and water.

The preferred acrylate polymers are derived from 0 to 20 mole percent of the acid monomers and from 80 to 100 mole percent of the alkyl ester monomers. Especially preferred monomers are:

n-butyl acrylate
n-butyl methacrylate
iso-butyl acrylate
iso-butyl methacrylate
sec-butyl acrylate
sec-butyl methacrylate
n-amyl acrylate
n-amyl methacrylate
iso-amyl acrylate
iso-amyl methacrylate
n-hexyl acrylate
n-hexyl methacrylate
cyclohexyl acrylate
2-ethylbutyl acrylate
2-ethylbutyl methacrylate
n-heptyl acrylate
n-heptyl methacrylate
n-octyl acrylate
n-octyl methacrylate
2-ethylhexyl acrylate
2-ethylhexyl methacrylate
iso-octyl acrylate
n-nonyl acrylate
n-nonyl methacrylate
n-decyl acrylate
n-decyl methacrylate
iso-decyl acrylate
iso-decyl methacrylate
undecyl methacrylate
lauryl acrylate
lauryl methacrylate
hexadecyl acrylate
hexadecyl methacrylate
octadecyl acrylate
octadecyl methacrylate
stearyl methacrylate
acrylic acid
methacrylic acid
ethacrylic acid
maleic acid
itaconic acid
β-carboxyethyl acrylate The preparation of the polymers from the olefinically unsaturated monomers is well documented in the literature and can be carried out by standard bulk, solution or emulsion techniques. Generally, the latter two are preferred with solution polymerization being most preferred. The polymerization of the monomers is catalyzed by free radical-generating catalysts such as peroxides, azo catalysts and the like. To be most effective, the reactor for such polymerization should be purged with an inert gas in order to remove traces of oxygen. The solution polymerizations are run in a compatable solvent and the final polymer solution preferably contains 25 to 60 percent solids.

The molecular weight of the acrylate polymers used in the compositions may vary over a broad range. The molecular weight must be suitably large to provide the requisite binding effect. The upper limit is determined only by formulation requirements. As the molecular weight increases, the polymers tend to become too viscous to formulate easily into cosmetically-appealing compositions. Generally, polymers having a Brookfield viscosity between 50 and 250,000 cps, and preferably between 1000 and 25,000 cps, when measured at 25 percent nonvolatiles, will be useful in the compositions of the invention.

The acrylate polymers useful in the compositions are insoluble in water and must have a solubility parameter between about 6–10 (cal/cc)$^{\frac{1}{2}}$ in poorly hydrogen-bonding solvents. The method for determining solubility parameter ranges of polymers and an extensive list of solvents (classified as either poorly hydrogen-bonding, moderately hydrogen-bonding, or strongly hydrogen-bonding) are described in *Polymer Handbook* (edited by Bandrup and Immergut), pages IV-344–358. Acrylate polymers having the requisite solubility parameter will be soluble in the emollient oil or oils.

The compositions of the invention are prepared in the conventional manner by first formulating the oil and water phases separately and mixing the two together. The oil phase ingredients are heated to about 180° F. (82° C.) or until the mixture appears clear. The emulsifying agent is then added to the oil phase (or it can be included in the initial mixture if it is lipophilic).

The water phase, which typically consists of water, humectants, thickeners and preservatives, is prepared by heating the ingredients (generally without the thickeners) to about 180° F. (82° C.). The thickeners are then slowly added, with stirring followed by heating the entire mixture to about 190°-200° F. (88°-93° C.).

The hot water phase is slowly added to the agitating oil phase until inversion occurs. The emollient oil of the compositions may be solid or liquid, but the entire formulation should be somewhat fluid at skin temperatures for ease of application. Fragrances, fillers, dyes, colorants, preservatives, antioxidants and other such materials conventionally used in moisturizing compositions may be included in minor amounts without affecting the substantivity of the compositions.

The major constituents of the oil phase is the emollient oil or mixture of oils. The oil phase contains about 0.5 to 20 percent by weight of the acrylate polymer, with the preferred range being from about 2 to 10 percent by weight. At levels below 0.5 percent, the polymer is less effective in holding a significant amount of the emollient oil on the skin when the skin is exposed to water. At levels above 20 percent, the formulation generally becomes sticky and unpleasant feeling.

The water phase preferably makes up about 45 to 95 percent by weight of the composition, and preferably 75 to 90 percent.

Any oil-in-water emulsifying agent conventionally used in cosmetic formulations may be used in the compositions of the present invention. It has been found, however, that the emulsifier can influence substantivity to some extent. Emulsifiers which provide good substantivity include the 82-mole ethoxylate of glyceryl tallowate, glyceryl stearate, and the 20-mole ethoxylate of cetyl/stearyl alcohol. The emulsifier is preferably present in an amount ranging from about 1 to 10 percent by weight of the composition and preferably, 2 to 4 percent by weight.

A preferred composition of the invention is illustrated as follows:

| Oil phase | |
|---|---|
| Acrylate Polymer (terpolymer of iso-octyl acrylate: stearyl methacrylate: acrylic acid, 50:40:10 mole ratio, 25% solids in iso-propyl palmitate, 8,400 cps) | 3.00% |
| Propylene Glycol Dicaprylate/Dicaprate[1] | 5.00% |
| 2 Mole Propoxylate of Myristyl Propionate | 2.00% |
| Petrolatum | 2.00% |
| Cetyl Palmitate[2] | 2.00% |
| Cetyl-Stearyl Alcohol | 1.00% |
| Propyl Paraben | 0.10% |
| Emulsifiers | |
| Glyceryl Stearate | 1.50% |
| 20 Mole Ethoxylate of Cetyl-Stearyl Alcohol[3] | 1.50% |
| Water phase | |
| Deionized Water | 80.15% |
| Magnesium Sulfate (Heptahydrate) | 0.50% |
| Xanthum Gum[4] | 0.50% |
| 10% Potassium Hydroxide In Water | 0.15% |
| 1,3-Dimethylol-5,5-Dimethyl Hydantoin | 0.30% |
| Methyl Paraben | 0.20% |
| Fragrance | 0.10% |

[1]"Lexol" PG865 (Inolex Corporation, Personal Care Division, Jackson & Swanson Sts., Philadelphia, PA 19148).
[2]"Waxenol" 816 (Wickhen Products, Inc., Big Pond Road, Huguenot, NY 12746)
[3]"Eumulgin" B-2 (Henkel Corporation, Chemical Specialties Division, 255 West Spring Valley Avenue, Maywood, NJ 07607)
[4]"Keltrol" (Kelco, Div. of Merck & Co., 8355 Aero Drive, San Diego, CA 92123

SUBSTANTIVITY TEST

The substantivity of the compositions of the invention is determined in-vivo by measuring the amount of applied emollient oil or oils present on a test site before and after a water assault. Basically, the method consists of subjecting a test subject's forearm containing the test composition to a water assault in which air bubbles are rising through a water bath and striking the test site. Subsequently, the site is extracted with alcohol to remove the remaining oils. These alcohol solutions are analyzed on a gas chromatograph for the amount of emollient oil or oils extracted. The latter can be compared to the theoretical amount of oil or oils applied and a percent retention calculated. Of course, the higher the percent retention (substantivity value), the more substantive is the test composition. Compositions of the present invention have a substantivity value of at least 30.

The steps used in carrying out the substantivity test are as follows:

1. The volar portion of the test subject's arm is washed with Ivory soap by passing lathered hands up and down the arm five times. The soap is rinsed from the arm, and the arm is dried with a clean cloth or paper towel.
2. The test subject is asked to sit in a chair with his/her arm resting on a horizontal arm rest. The palm of the hand is facing upward and the elbow is bent at a 90° angle.
3. Using a 6×12 cm template, a rectangular test site is marked off of the broadest portion of the subject's lower arm.
4. A grease barrier (Apiezon N, Apiezon Products Ltd., London) is carefully placed around the marked test site to prevent spreading of the test composition.
5. An 80 µl aliquot of the test composition (40 µl if only the oil phase is tested) is applied to the lower half of the test site and spread evenly and thoroughly over the lower half of the 6×12 area using a clean glass rod. Another 80 µl aliquot of the same test composition is applied in the same manner to the upper half of the 6×12 cm area.
6. The test composition is allowed to equilibrate on the test site for 5 minutes. During this period a water bath is filled with 35° C. (95° F.) water and an aerator[1] is placed in the center of the bath. The air is turned on at a pressure of 2.0 psi to the aerator (1.0 psi when the oil phase only is being evaluated).

[1]6×12×3 cm plexiglass box equipped with a 6×12 cm "3M Brand Porous Structure" Grade 15 and an air line.

7. The arm is placed in a horizontal position in the bath with the volar portion of the arm facing down over the air bubbles. The arm is moved back and forth across the bubbles so that the bubbles move from one side of the test site to the other and back again. This procedure is followed for a total of 4 minutes. (When the oil phase only is evaluated, the arm is placed in a horizontal position with the volar portion of the arm facing down into the bath and close to the near bath wall. The arm is moved slowly over the air bubbles to the other side of the bath and then slowly brought back across the bubbles. This procedure is repeated so that the arm passes over the bubbles for a total of 10 passes in one minute).

8. The arm is removed from the water bath and the area around the test site is towel-dried. A stream of air (compressed) is used to gently blow the water drops from the test site.

9. Five minutes after the arm is removed from the water bath, the test site is extracted at two locations with the subject's arm in the same position as in step 1. One end of a hollow glass cylinder 25 mm long and having an inside diameter of 40 mm is lubricated with a thin layer of Apiezon N grease to prevent solvent leakage. This end of the cylinder is pressed onto the lower portion of the test site by the subject. Ten (10.0) ml of isopropyl alcohol (IPA) is poured into the cylinder on the test site. The IPA is agitated by using a 10 ml disposable syringe to withdraw and discharge the solvent in the glass cylinder. The force of the discharged solvent is directed at different locations each time. After eleven such cycles, the IPA is removed completely and placed in a container which is tightly capped. The glass cylinder is carefully removed so as not to allow any residual solvent to run into the other half of the test site. The extracted side is wiped dry with a tissue and then the upper site extracted with fresh IPA as above.

10. When the glass cylinder is pressed firmly against the arm to prevent solvent leakage, the underlying tissue puckers up into the center of the cylinder. To relieve this stress, the skin appear to stretch, and it stretches more in one direction than in the other. When the cylinder is removed an elliptical indentation remains on the skin surface showing exactly where the test site was extracted. To determine the area of this extracted site, the inner major and minor axes of the elliptical indentation are measured (in hundredths of a centimeter). These diameters are recorded for future calculations.

11. The water bath is emptied and wiped with a paper towel in order to remove any oil which may adhere to the wall before subsequent tests are conducted.

GAS CHROMATOGRAPHIC ANALYSIS

A Hewlett Packard 5880A gas chromatograph equipped with "Level Four Temperature Programming", "Integrator and Methods", an automatic sampler and a 25 m×0.3 mm (ID) SE-54 silicone capillary column is used. The following procedure is employed.

1. Three standard samples approximately 0.2500 g, 0.0500 g, and 0.0050 g, respectively, of the test composition (or half of these amounts when the oil phase is analyzed) are weighed. Approximately 50 g of isopropyl alcohol are added to solubilize each sample, and the resulting solution is weighed. The percent of total composition for each of these standard solutions is calculated (alternatively, the percent oil or percent of one particular oil may be calculated).

2. The standard solutions are analyzed on the gas chromatograph using conditions which give reasonable separation of the emollient oils. This will vary depending on temperature, flow rates, etc.

3. A calibration table is set up on the gas chromatograph by dividing the calculated percent total composition (or oil phase or emollient oil) in the standard solutions by their respective chromatographic integrated area. If a calibration curve is used, the percent of total composition for each standard solution is plotted against its respective chromatographic integrated area.

4. The extraction samples obtained in step 9 of the Substantivity Test above are run on the chromatograph after their respective standard solutions. The chromatograph will print out the percent total composition (or oil phase or emollient oil) by comparing the extraction sample's area to the stored calibration table for each standard solution. Alternatively, the extraction sample's areas are compared with those of an external calibration table or curve and the percent total composition (or oil phase or emollient oil) is determined.

CALCULATIONS

The percent retention of the emollient oils (substantivity value) for each sample formulation is calculated using the following formula:

$$\text{percent retention} = \frac{(\text{constant}) \times (\% \text{ total composition in extraction sample})}{\text{area extracted} \times \text{amount of total composition originally applied}}$$

where: % total composition in the extraction sample is determined by the gas chromatograph;

$$\text{area extracted} = \frac{c_1 d_1 + c_2 d_2}{8}$$

where c's and d's are the major and minor axes respectively of the extraction sites on the arm; amount of total composition originally applied = amount applied to each 6×6 cm portion of the 6×12 cm test site (for oils, this is 40 $\mu$l and for lotions 80 $\mu$l).

The constant in the formula is 313255 $\mu$lcm$^2$.

The percent retention of the emollient oils (substantivity value) in Table III below is calculated using the following formula in which the emollient oil-isopropyl palmitate (IPP) was used to quantitate the system and 40 $\mu$l of solution was applied per 6×6 cm test site.

$$\text{percent retention} = \frac{(\text{constant}) \times (\% \text{ IPP in extraction sample})}{(\% \text{ IPP in oil composition originally applied}) \times (\text{area extracted})}$$

where: % IPP in extraction sample = percent isopropyl palmitate in the extraction sample determined by the gas chromatography; area extracted = as above; and the constant = 829648 $\mu$lcm$^2$.

In this manner, a percent retention can be determined for test compositions and their controls (without acrylate polymers) which were run at the same time on different arms of each test subject.

A number of compositions of the invention were tested according to the substantivity test described above. Unless otherwise indicated, the ingredients listed in the following Table I were used in these compositions.

TABLE I

| CHEMICAL OR COMMON NAME | TRADE NAME | SUPPLIER | ADDRESS |
| --- | --- | --- | --- |
| 2 mole propoxylate of myristyl propionate | Crodamol PMP | Croda, Inc. | 51 Madison Ave. New York, NY 10010 |
| Isopropyl Palmitate | Unimate IPP | Union Camp Corp. Chemical Division | 1600 Valley Road Wayne, NJ 07470 |
| Dicapryl Adipate | Unimate 600 | Union Camp Corp. Chemical Division | 1600 Valley Road Wayne, NJ 07470 |
| Mineral Oil (65/75) | Carnation White Mineral Oil | Witco Chemical Sonneborn Div. | 277 Park Ave. New York, NY 10017 |
| 15 mole Propoxylate of Stearyl Alcohol | Arlamol E | ICI America, Inc. | Wilmington, DE 19897 |
| Petrolatum (USP White) | Amojel Petrolatum Snow White | Amoco Oil Co. | Chicago, IL 60680 |
| Cetyl Alcohol (synthetic) | Adol 520NF | Sherex Chemical Co. | P.O. Box 646 Dublin, OH 43017 |
| Cetyl-Stearyl Alcohol | Adol 63 | Sherex Chemical Co. | P.O. Box 646 Dublin, OH 43017 |
| Coconut Oil (m.p. = 76° F., 24° C.) | Cobee 76 | PVO Int'l, Inc. | 416 Division St. Boonton, NJ 07005 |
| Cocoa Butter (U.S.P.) | — | Woodward & Dickerson | Two Girard Plaza Philadelphia, PA 19102 |
| Polydimethylsiloxane Polymer (50 cst., 100 cst.) | Dow Corning 200 Fluid | Dow Corning Corp. | Midland, MI 48640 |
| $C_{12-15}$ Alcohols Benzoate | Finsolv TN | Fintex, Inc. | 418 Falmouth Ave. Elmwood Park, NJ 07407 |
| Glyceryl Stearate | Emerest 2400 | Emery Ind., Inc. | 1501 West Elizabeth Ave. Linden, NJ 07036 |
| Stearic Acid | Emersol 132 | Emery Ind., Inc. | 4900 Este Ave. Cincinnati, OH 45232 |
| Sorbitan Monostearate | Span 60 | ICI Americas, Inc. | Wilmington, DE 19897 |
| Polysorbate 60 (20 Mole Ethoxylate of Sorbitan Monostearate) | Tween 60 | ICI Americas, Inc. | Wilmington, DE 19897 |
| 82 mole Ethoxylate of Glyceryl Tallowate | Varonic LI 48 | Sherex Chem. Co., Inc. | P.O. Box 646 Dublin, OH 43017 |
| Propylene Glycol, U.S.P. | — | Union Carbide Corp. and Olin Chemicals | 270 Park Ave. New York, NY 10017 120 Long Ridge Road Stamford, CT 06904 |
| Glycerine, U.S.P. | — | Emery Ind., Inc. | 4900 Este Ave. Cincinnati, OH 45232 |
| Hydroxyethylcellulose | Natrosol 250HR | Hercules, Inc. | Wilmington, DE 19899 |
| Colloidal Magnesium Aluminum Silicate | Veegum | R. T. Vanderbilt Co. | 30 Winfield St. Norwalk, CT 06855 |
| Carboxy Vinyl Polymer | Carbopol 934 | B. F. Goodrich Chem. Division | 6100 Oak Tree Blvd. Cleveland, OH 44131 |
| Aloe Vera Gel | Aloe Vera Gel | Terry Corporation & Aloe Laboratories of Texas | 110 Tomahawk Drive Indian Harbour Beach, FL 32937 Route 1 - Box 161 Lyford, TX 78569 |
| Propyl Paraben | Lexgard P | Inolex Corp. Personal Care Div. | Jackson & Swanson Sts. Philadelphia, PA 19148 |
| Methyl Paraben | Lexgard M | Inolex Corp. Personal Care Div. | Jackson & Swanson Sts. Philadelphia, PA 19148 |
| 1,3-Dimethylol-5,5 Dimethyl Hydantoin | Glydant | Clyco Chem., Inc. | 51 Weaver St. Greenwich, CT 08830 |
| Mineral Oil (345/355) | Kaydol White Mineral Oil | Witco Chemical Sonneborn Div. | 227 Park Ave. New York, NY 10017 |
| Acetylated Lanolin | Modulan | Amerchol | Amerchol Park Edison, NJ 08817 |
| Peanut Oil | — | Durkee Industrial | 900 Union Commerce Bldg. Cleveland, OH 44115 |
| Palm Kernal Oil (Partially hydrogenated) | Paramount B | Durkee Industrial | 900 Union Commerce Bldg. Cleveland, OH 44115 |
| 2-Ethylhexyl Palmitate | Ceraphyl 368 | Van Dyke & Co., Inc. | Main and Williams Streets Belleville, NJ 07109 |

The preparation procedure for each composition tested was as follows:

All oil phase ingredients were added to one stainless steel vessel and heated to about 180° F. (82° C.) on a steam bath with slow stirring. After the oil phase appeared clear, the emulsifier was added.

The water phase ingredients, including water, propylene glycol and preservatives were mixed together in a separate stainless steel vessel and heated to about 180° F. (82° C.) on a steam bath. The thickeners were added slowly and the entire mixture was stirred for about 5 minutes and then heated to 190°-200° F. (88°-93° C.).

The water phase (190°-200° F.) was slowly added to the agitating oil phase over a 3 to 5 minute period, while maintaining the emulsion at about 180° F. (82° C.). The rate of agitation was gradually increased as the water phase was added to maintain efficient mixing. The water was added more slowly initially until inversion occurs. The empty vessel was rinsed with a small amount of water, heated and the water was added to the emulsion. Stirring and heating of the emulsion were continued for a few minutes (at 180° F.).

The steam was turned off and stirring continued while the emulsion gradually cooled. When it had cooled to 140° F. (60° C.), aloe vera gel was added if desired. When the batch had cooled to 110°-120° F. (43°-49° C.), the fragrance oil was added. Stirring was continued until it had cooled to near room temperature.

EXAMPLE 1

|  | W/W % |
|---|---|
| Acrylate Polymer* | 3.00 |
| 2 Mole Propoxylate of Myristyl Propionate | 2.50 |
| Isopropyl Palmitate | 2.25 |
| Mineral Oil (65/75) | 2.00 |
| Dicapryl Adipate | 2.00 |
| 15 Mole Propoxylate of Stearyl Alcohol | 1.50 |
| Cetyl-Stearyl Alcohol | 0.85 |
| Coconut Oil (m.p. = 76° F., 24° C.) | 0.65 |
| Cocoa Butter | 0.25 |
| Polydimethylsiloxane Polymer (50 cst) | 0.25 |
| Propyl Paraben | 0.10 |
| 82 Mole Ethoxylate of Glyceryl Talloate | 3.00 |
| Deionized Water | 72.50 |
| Propylene Glycol | 3.00 |
| Aloe Vera Gel | 3.00 |
| Colloidal Magnesium Aluminum Silicate | 2.00 |
| Hydroxyethylcellulose | 0.50 |
| 1,3-Dimethylol-5,5-Dimethyl Hydantoin | 0.30 |
| Methyl Paraben | 0.20 |
| Fragrance | 0.15 |

*Copolymer of iso-octyl acrylate:acrylic acid, 90:10 mole ratio, 25% solids in isopropyl palmitate (IPP), 6,370 cps

EXAMPLE 2

| Acrylate Polymer* | 6.00 |
|---|---|
| 2 Mole Propoxylate of Myristyl Propionate | 2.50 |
| Mineral Oil (65/75) | 2.00 |
| Dicapryl Adipate | 2.00 |
| 15 Mole Propoxylate of Stearyl Alcohol | 1.50 |
| Cetyl-Stearyl Alcohol | 0.85 |
| Coconut Oil (m.p. = 76° F., 24° C.) | 0.65 |
| Cocoa Butter | 0.25 |
| Polydimethylsiloxane Polymer (50 cst) | 0.25 |
| Propyl Paraben | 0.10 |
| 82 Mole Ethoxylate of Glyceryl Talloate | 3.00 |
| Deionized Water | 71.75 |
| Propylene Glycol | 3.00 |
| Aloe Vera Gel | 3.00 |
| Colloidal Magnesium Aluminum Silicate | 2.00 |
| Hydroxyethylcellulose | 0.50 |
| 1,3-Dimethylol-5,5-Dimethyl Hydantoin | 0.30 |
| Methyl Paraben | 0.20 |
| Fragrance | 0.15 |

*Copolymer of iso-octyl acrylate:acrylic acid, 90:10 mole ratio, 25% solids in isopropyl palmitate 6,370 cps

EXAMPLE 3

| Acrylate Polymer (Copolymer of iso-octyl acrylate: stearyl methacrylate, 50:50 mole ratio, 25% solids in IPP, 7,020 cps) | 6.00% |
|---|---|

All other ingredients and proportions were identical to those in Example 2.

EXAMPLE 4

| Acrylate Polymer (Terpolymer of iso-octyl acrylate: stearyl methacrylate:acrylic acid, 50:40:10 mole ratio, 25% solids in IPP, 10,260 cps) | 3.00% |
|---|---|

All other ingredients and proportions were identical to those in Example 1.

EXAMPLE 5

| Acrylate Polymer (Terpolymer of iso-octyl acrylate: stearyl methacrylate:acrylic acid, 50:40:10 mole ratio, 25% solids in IPP, 2,160 cps) | 6.00% |
|---|---|

Aloe Vera Gel

All other ingredients and proportions were identical to those in Example 2.

EXAMPLE 6

| Acrylate Polymer (Terpolymer of iso-octyl acrylate: stearyl methacrylate:acrylic acid, 50:40:10 mole ratio, 25% solids in IPP, 6,370 cps) | 6.00% |
|---|---|

All other ingredients and proportions were identical to those in Example 2.

EXAMPLE 7

| Acrylate Polymer (Terpolymer of iso-octyl acrylate: stearyl methacrylate:acrylic acid, 50:40:10 mole ratio, 25% solids in IPP, 10,760 cps) | 6.00% |
|---|---|

Aloe Vera Gel

All other ingredients and proportions were identical to those in Example 2.

EXAMPLE 8

| Acrylate Polymer (Terpolymer of iso-octyl acrylate: stearyl methacrylate:acrylic acid, 50:40:10 mole ratio, 25% solids in IPP, 24,250 cps) | 6.00% |
|---|---|

Aloe Vera Gel

All other ingredients and proportions were identical to those in Example 2.

EXAMPLE 9

| Acrylate Polymer (Terpolymer of iso-octyl acrylate: stearyl methacrylate:acrylic acid, 50:30:20 mole ratio, 25% solids in IPP, 10,900 cps) | 6.00% |
|---|---|

All other ingredients and proportions were identical to those in Example 2.

EXAMPLE 10

| Acrylate Polymer (Terpolymer of iso-octyl acrylate: stearyl methacrylate:acrylic acid, 10:70:20 mole ratio, 25% solids in IPP, 13,360 cps) | 3.00% |
|---|---|

All other ingredients and proportions were identical to those in Example 1.

EXAMPLE 11

| | |
|---|---|
| Acrylate Polymer (Terpolymer of iso-octyl acrylate: stearyl methacrylate:acrylic acid, 10:70:20 mole ratio, 25% solids in IPP, 13,360 cps) | 6.00% |

All other ingredients and proportions were identical to those in Example 2.

EXAMPLE 12

| | |
|---|---|
| Acrylate Polymer (Terpolymer of iso-octyl acrylate:stearyl methacrylate:acrylic acid 50:40:10 mole ratio, 25% solids in IPP, 10,260 cps) | 0.52% |
| Isopropyl Palmitate | 9.26% |
| Mineral Oil (65/75) | 1.00% |
| Cetyl-stearyl Alcohol | 0.85% |
| 15 Mole Propoxylate of Stearyl Alcohol | 0.52% |
| Dicapryl Adipate | 0.52% |
| Cocoa Butter | 0.25% |
| Propyl Paraben | 0.10% |
| Sorbitan Monosterate | 0.83% |
| 20 Mole Ethoxylate of Sorbitan Monostearate | 2.17% |
| Deionized Water | 79.38% |
| Propylene Glycol | 2.99% |
| Hydroxyethylcellulose | 1.00% |
| 1,3-Dimethylol-5,5-Dimethyl Hydantoin | 0.30% |
| Methyl Paraben | 0.20% |
| Fragrance | 0.15% |

EXAMPLE 13

| | |
|---|---|
| Acrylate Polymer (Terpolymer of iso-octyl acrylate:stearyl methacrylate:acrylic acid, 50:40:20 mole ratio, 25% solids in IPP, 6,370 cps) | 3.08% |
| 2 Mole Propoxylate of Myristyl Propionate | 7.18% |
| Petrolatum | 2.05% |
| Cetyl-Stearyl alcohol | 2.05% |
| Propyl Paraben | 0.11% |
| Sorbitan Monostearate | 0.85% |
| 20 Mole Ethoxylate of Sorbitan Monostearate | 2.22% |
| Deionized Water | 78.90% |
| Glycerine | 2.05% |
| 10% Potassium Hydroxide in Water | 0.74% |
| Carboxyl Vinyl Polymer | 0.26% |
| 1,3-dimethylol-5,5-Dimethyl Hydantoin | 0.31% |
| Methyl Paraben | 0.21% |

EXAMPLE 14

| | |
|---|---|
| Acrylate Polymer (Terpolymer of iso-octyl acrylate:stearyl methacrylate:acrylic acid, 50:40:00 mole ratio, 25% solids in IPP, 10,760 cps) | 6.00% |
| Isopropyl Palmitate | 5.17% |
| Deionized Water | 77.99% |

All other ingredients and proportions were identical to those in Example 12.

EXAMPLE 15

| | |
|---|---|
| Acrylate Polymer (Terpolymer of iso-octyl acrylate:stearyl methacrylate:acrylic acid, 50:40:10 mole ratio, 25% solids in IPP, 10,260 cps) | 12.84% |
| Deionized Water | 76.37% |

All other ingredients and proportions were identical to those in Example 12.

EXAMPLE 16

| | |
|---|---|
| Acrylate Polymer (Terpolymer of iso-octyl acrylate:stearyl methacrylate:acrylic acid, 50:30:20 mole ratio, 25% solids in IPP, 10,900 cps) | 4.14% |
| Mineral Oil | 3.10% |
| 2 Mole Propoxylate of Myristyl Propionate | 3.10% |
| $C_{12-15}$ Alcohols Benzoate | 2.07% |
| Cetyl Alcohol | 1.03% |
| Polydimethylsiloxane Polymer (100 cst) | 0.52% |
| Propyl Paraben | 0.10% |
| Sorbitan Monostearate | 0.86% |
| 20 Mole Ethoxylate of Sorbitan Monostearate | 2.24% |
| Deionized Water | 76.94% |
| Propylene Glycol | 5.17% |
| 1,3-Dimethylol-5,5-Dimethyl Hydantoin | 0.31% |
| Methyl Paraben | 0.21% |
| Fragrance | 0.21% |

EXAMPLE 17

| | |
|---|---|
| Acrylate Polymer (Terpolymer of iso-octyl acrylate:stearyl methacrylate:acrylic acid, 50:30:20 mole ratio, 25% solids in IPP, 10,900 cps) | 4.00% |
| Mineral Oil (65/75) | 3.00% |
| 2 Mole Propoxylate of Myristyl Propionate | 3.00% |
| $C_{12-15}$ Alcohols Benzoate | 2.00% |
| Stearic Acid | 1.00% |
| Glyceryl Stearate | 1.00% |
| Cocoa Butter | 1.00% |
| Coconut Oil (m.p. = 76° F., 24° C.) | 1.00% |
| Polydimethylsiloxane Polymer (50 cst) | 0.50% |
| Propyl Paraben | 0.10% |
| 82 Mole Ethoxylate of Glyceryl Talloate | 3.00% |
| Deionized Water | 71.11% |
| Propylene Glycol | 5.00% |
| Aloe Vera Gel | 3.12% |
| Colloidal Magnesium Aluminum Silicate | 1.00% |
| 10% Potassium Hydroxide in Water | 0.37% |
| Carboxy Vinyl Polymer | 0.25% |
| 1,3-Dimethylol-5,5-Dimethyl Hydantoin | 0.30% |
| Methyl Paraben | 0.20% |
| Fragrance | 0.05% |

EXAMPLE 18

| | |
|---|---|
| Acrylate Polymer (Terpolymer of iso-octyl acrylate:stearyl methacrylate:acrylic acid, 50:30:20 mole ratio, 25% solids in IPP, 10,900 cps) | 4.14% |
| Mineral Oil (65/75) | 3.12% |
| 2 Mole Propoxylate of Myristyl Propionate | 3.12% |
| $C_{12-15}$ Alcohols Benzoate | 2.08% |
| Cetyl Alcohol | 1.04% |
| Polydimethylsiloxane Polymer (100 cst) | 0.52% |
| Propyl Parben | 0.10% |
| Stearic Acid | 4.16% |
| 10% Potassium Hydroxide in Water | 2.58% |
| Deionized Water | 73.06% |
| Propylene Glycol | 5.21% |
| 1,3-Dimethylol-5,5-Dimethyl Hydantoin | 0.31% |
| Methyl Paraben | 0.21% |
| Fragrance | 0.31% |

The substantivity values of the compositions of Examples 1-18 are set forth in the following Table II.

TABLE II

SUBSTANTIVITY VALUES

| Example Number | Polymer Monomers | Mole Ratio | Viscosity[2] (Cps) | Percent Polymer in Oil Phase | Surfactant | Substantivity Value[1] Test Composition | Control[3] |
|---|---|---|---|---|---|---|---|
| 1 | 10A[4]:AA[5] | 90:10 | 6,370 | 4.9 | Varionic L148[6] | 70 | 11 |
| 2 | 10A:AA | 90:10 | 6,370 | 9.3 | Varionic L148 | 85 | 7 |
| 3 | 10A:SMA[7] | 50:50 | 7,020 | 9.3 | Varionic L148 | 76 | 8 |
| 4 | 10A:SMA:AA | 50:40:10 | 10,760 | 4.9 | Varionic L148 | 66 | 11 |
| 5 | 10A:SMA:AA | 50:40:10 | 2,160 | 9.3 | Varionic L148 | 54 | 8 |
| 6 | 10A:SMA:AA | 50:40:10 | 6,370 | 9.3 | Varionic L148 | 85 | 9 |
| 7 | 10A:SMA:AA | 50:40:10 | 10,760 | 9.3 | Varionic L148 | 93 | 16 |
| 8 | 10A:SMA:AA | 50:40:10 | 24,250 | 9.3 | Varionic L148 | 97 | 10 |
| 9 | 10A:SMA:AA | 50:30:20 | 10,900 | 9.3 | Varionic L148 | 96 | 14 |
| 10 | 10A:SMA:AA | 10:70:20 | 13,360 | 4.9 | Varionic L148 | 76 | 7 |
| 11 | 10A:SMA:AA | 10:70:20 | 13,360 | 9.3 | Varionic L148 | 93 | 14 |
| 12 | 10A:SMA:AA | 50:40:10 | 10,760 | 1.0 | Span60[8]-Tween60[9] | 40 | 24 |
| 13 | 10A:SMA:AA | 50:40:10 | 6,370 | 5.3 | Span60-Tween60 | 55 | 29 |
| 14 | 10A:SMA:AA | 50:40:10 | 10,760 | 10.0 | Span60-Tween60 | 63 | 23 |
| 15 | 10A:SMA:AA | 50:40:10 | 10,760 | 20.0 | Span60-Tween60 | 92 | 21 |
| 16 | 10A:SMA:AA | 50:30:20 | 10,900 | 6.9 | Span60-Tween60 | 36 | 19 |
| 17 | 10A:SMA:AA | 50:30:20 | 10,900 | 6.0 | Potassium Stearate & Glycerol Monostearate | 51 | 22 |
| 18 | 10A:SMA:AA | 50:30:20 | 10,900 | 5.0 | Potassium Stearate | 44 | 8 |

[1]Retention of amount applied to the extraction site
[2]Brookfield viscosity 25% polymer in isopropyl palmitate
[3]Control formulation - no polymer
[4]iso-Octyl acrylate
[5]Acrylic acid
[6]82 mole Ethoxylate of glyceryl tallowate
[7]Stearyl methacrylate
[8]Sorbitan monostearate
[9]20 mole Ethoxylate of sorbitan monostearate To further determine the ability of the acrylate polymer to retain emollient oils on the skin, a number of test compositions comprising only the oil phase of the emulsions were tested in the substantivity test. The oil phase used in all cases was as follows.

| CONTROL OIL PHASE | Weight % |
|---|---|
| Mineral Oil (65/75 cps) | 30.9 |
| Mineral Oil (345-355 cps) | 12.4 |
| Isopropyl Palmitate | 20.3 |

| -continued CONTROL OIL PHASE | Weight % |
|---|---|
| Coconut Oil (mp 76° F.) | 15.5 |
| Cocoa Butter | 1.0 |
| Acetylated Lanolin | 1.0 |
| Peanut Oil | 5.2 |
| Partially Hydrogenated Palm Kernel Oil | 5.2 |
| 2 Mole Propoxylate of Myristyl Propionate | 4.1 |
| 2-Ethylhexyl Palmitate | 4.1 |
| Propyl Paraben | .3 |
| | 100 parts |

TABLE III

| COMPOSITION NUMBER | POLYMER MONOMERS | MOLE RATIO | VISCOSITY (Cps)[2] | SOLVENT | SUBSTANTIVITY VALUE[1] POLYMER[3] | CONTROL[4] |
|---|---|---|---|---|---|---|
| 1 | BA[5] | 100 | 2120[6] | DCA[7] | 57.6 | 21.6 |
| 2 | 10A[8] | 100 | 2112 | EOB[9] | 39.7 | 12.8 |
| 3 | EHA[10] | 100 | 392[6] | EOB | 62.2 | 13.7 |
| 4 | LMA[11] | 100 | 1324 | EOB | 30.2 | 9.1 |
| 5 | SMA[12] | 100 | 2590 | EOB | 25.8 | 16.3 |
| 6 | BA:AA[13] | 90:10 | 2810[6] | DCA | 67.3 | 13.7 |
| 7 | 10A:AA | 90:10 | 5500 | EOB | 66.9 | 5.4 |
| 8 | 10A:AA | 90:10 | 2700 | EOB | 66.0 | 10.8 |
| 9 | EHA:AA | 90:10 | 774[6] | EOB | 100.0 | 22.8 |
| 10 | 10A:maleic acid | 95:5 | 748[6] | EOB | 85.9 | 13.3 |
| 11 | 10A:nVP[14] | 95:5 | 516[6] | DCA | 47.8 | 12.1 |
| 12 | LMA:nVP | 87.5:12.5 | 454 | EOB | 22.6 | 8.2 |
| 13 | IOA:SMA | 90:10 | 2640 | EOB | 70.2 | 15.7 |
| 14 | 10A:SMA | 70:30 | 5540 | EOB | 63.0 | 8.3 |
| 15 | 10A:SMA | 50:50 | 7020 | EOB | 67.9 | 8.2 |
| 16 | 10A:SMA | 30:70 | 17760 | EOB | 96.2 | 7.9 |
| 17 | 10A:nVP:HEA[15] | 89:10:1 | 516[16] | EOB | 44.1 | 8.3 |
| 18 | SMA:BA:AA | 70:20:10 | 3390 | EOB | 29.8[19] | 11.0 |
| 19 | 10A:SMA:AA | 70:10:20 | 13680 | EOB | 50.4 | 12.5 |
| 20 | 10A:SMA:AA | 60:30:10 | 5400 | EOB | 51.9 | 10.7 |
| 21 | 10A:SMa:AA | 60:20:20 | 10600 | EOB | 24.6 | 8.3 |
| 22 | 10A:SMA:AA | 50:40:10 | 6370 | EOB | 65.2 | 8.9 |
| 23 | 10A:SMA:AA | 50:40:10 | 1970 | EOB | 34.5 | 13.5 |
| 24 | 10A:SMA:AA | 50:30:20 | 10700 | EOB | 58.0 | 10.8 |
| 25 | 10A:SMA:AA | 50:20:30 | 225000 | EOB | 38.5 | 11.9 |
| 26 | 10A:SMA:AA | 50:20:30 | 20850 | EOB | 21.2 | 13.6 |

TABLE III-continued

| COMPOSITION NUMBER | POLYMER MONOMERS | MOLE RATIO | VISCOSITY (Cps)[2] | SOLVENT | SUBSTANTIVITY VALUE[1] POLYMER[3] | CONTROL[4] |
|---|---|---|---|---|---|---|
| 27 | 10A:SMA:AA | 40:50:10 | 14000 | EOB | 57.2 | 15.7 |
| 28 | 10A:SMA:AA | 40:40:20 | 10640 | EOB | 47.7 | 9.4 |
| 29 | 10A:SMA:AA | 40:30:30 | 218500 | EOB | 41.3 | 7.3 |
| 30 | 10A:SMA:AA | 30:50:20 | 12180 | EOB | 40.9 | 7.2 |
| 31 | 10A:SMA:AA | 20:60:20 | 11920 | EOB | 43.8 | 7.5 |
| 32 | 10A:SMA:AA | 10:70:20 | 13360 | EOB | 65.3 | 12.4 |
| 33 | 10A:SMA:AA | 10:70:20 | 21400 | EOB | 100.0 | 10.5 |
| 34 | 10A:SMA:AA | 10:80:10 | 6570 | EOB | 60.2 | 12.3 |
| 35 | EA[17]:BA:EHA:AA | 10:40:40:10 | 3912[6] | DCA | 100.0 | 15.4 |
| 36 | EA:BA:EHA:MAA[18] | 10:40:40:10 | 2184[6] | DCA | 80.0 | 10.0 |
| 37 | 10A:SMA:AA | 50:40:10 | 6370 | EOB | 29.0[19] | 10.9 |
| 38 | 10A:SMA:AA | 50:40:10 | 6370 | EOB | 100.0[20] | 9.3 |
| 39 | 10A:ODA[21]:AA | 40:40:20 | | EOB | 38.6 | 14.3 |

[1]Percent retention compared to theoretical amount placed on extraction site
[2]Brookfield viscosity, 25% polymer in isopropyl palmitate
[3]Oil phase plus 2% by weight polymer
[4]Oil phase without polymer
[5]Butyl acrylate
[6]25% polymer in ethyl acetate
[7]Dicapryl adipate
[8]Iso-octyl acrylate
[9]Emollient oil base
[10]2-Ethylhexyl acrylate
[11]Lauryl methacylate
[12]Stearyl methacylate
[13]Acrylic acid
[14]n-Vinyl pyrrolidone
[15]Hydroxyethyl acrylate
[16]25% polymer in toluene
[17]Ethyl acrylate
[18]Methacrylic acid
[19]0.5% polymer
[20]6.77% polymer
[21]Octadecyl acrylate

What is claimed is:

1. A moisturizing composition for application to mammalian skin consisting essentially of an oil-in water emulsion containing:

(a) an oil phase comprising an effective amount of at least one emollient oil and from 0.5 to 20 percent by weight of an acrylate polymer having a solubility parameter of 6 to 10 $(cal/cc)^{\frac{1}{2}}$ in poorly hydrogen-bonding solvents, said polymer being derived from the same or different ester monomers of the formula:

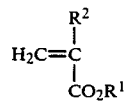

wherein $R^1$ is an alkyl radical containing 4 to 18 carbon atoms in cyclic, straight- or branched-chain configuration; $R^2$ is hydrogen or lower alkyl, and up to 30 mole percent of the same or different monomers of the formula:

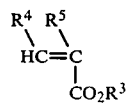

wherein $R^3$ is H or an alkyl radical containing 1 to 18 carbon atoms; $R^4$ is hydrogen, methyl, or $-CO_2R^3$ and $R^5$ is hydrogen, lower alkyl or $-CH_2CO_2R^3$; provided, that when $R^4$ is not hydrogen, $R^5$ is hydrogen, and when $R^5$ is not hydrogen, $R^4$ is hydrogen, (b) about 45 to 95 percent by weight of a water phase, and (c) an effective amount of an emulsifying agent, said composition having a substantivity value of at least 30.

2. The composition according to claim 1 wherein said ester monomer is an alkyl ester of acrylic acid or methacrylic acid.

3. The composition according to claim 1 wherein said acrylate polymer is selected from the group consisting of:

a copolymer of iso-octyl acrylate and acrylic acid;

a copolymer of iso-octyl acrylate and stearyl methacrylate; and a terpolymer of iso-octyl acrylate, stearyl methacrylate and acrylic acid.

4. The composition according to claim 1 wherein said emulsifying agent is present in an amount between 1 and 10 percent by weight of said composition.

5. The composition according to claim 1 wherein said emulsifying agent is selected from the group consisting of:

82-mole ethoxylate of glyceryl tallowate glyceryl stearate, and the 20-mole ethoxylate of cetyl/stearyl alcohol.

6. A method of moisturizing mammalian skin comprising applying to said skin an effective amount of a composition comprising an oil-in-water emulsion containing an oil phase comprising an effective amount of at least one emollient oil and from 0.5 to 20 percent by weight of an acrylate polymer having a solubility parameter of 6 to 10 $(cal/cc)^{\frac{1}{2}}$ in poorly hydrogen-bonding solvents, about 45 to 95 percent by weight of a water phase and, an effective amount of an emulsifying agent, said composition having a substantivity value of at least 30.

* * * * *